United States Patent [19]

Ebner

[11] 4,415,482

[45] Nov. 15, 1983

[54] OXIDATION AND AMMOXIDATION CATALYST

[75] Inventor: Jerry R. Ebner, St. Charles, Mo.

[73] Assignee: Monsanto Company, Del.

[21] Appl. No.: 320,403

[22] Filed: Nov. 12, 1981

[51] Int. Cl.³ .................. B01J 29/16; B01J 21/02; B01J 27/14; B01J 27/02

[52] U.S. Cl. .................. 502/205; 502/209; 502/215; 502/242; 502/244; 502/248; 502/309; 502/312

[58] Field of Search ............. 252/432, 435, 437, 439, 252/468, 456, 469

[56] References Cited

U.S. PATENT DOCUMENTS

| | | | |
|---|---|---|---|
| 3,681,421 | 8/1972 | Barclay et al. | 260/465.3 |
| 4,040,978 | 8/1977 | Li | 252/470 X |
| 4,062,885 | 12/1977 | Mekhtiev et al. | 260/465 |
| 4,093,558 | 6/1978 | Grasselli et al. | 252/435 X |
| 4,148,757 | 4/1979 | Brazdil et al. | 252/439 X |
| 4,212,766 | 7/1980 | Brazdil et al. | 252/439 X |

FOREIGN PATENT DOCUMENTS 32012 12/1980 European Pat. Off. .
32618 12/1980 European Pat. Off. .

Primary Examiner—William G. Wright
Attorney, Agent, or Firm—Richard D. Stone; A. Milton Cornwell; Roger R. Jones

[57] ABSTRACT

Disclosed herein are catalysts useful for oxidation and ammoxidation of hydrocarbons. Such catalysts have the empirical formula $$BiMo_aV_bSb_cM_dO_x$$

wherein a is 0.5-2, b is 0.01-0.12, c is 0.01-10, d is 0-0.5 and x is selected to satisfy the valence requirements of the other elements present. In such catalysts, M is one or more elements selected from Groups I-A, II-A, III-A, V-A, VI-A, I-B, IV-B, VI-B and VII-B of the Periodic Table.

Catalysts according to the invention are prepared by forming a slurry of a vanadium component, an antimony component, a hydrophilic bismuth molybdate component having the empirical formula $$BiMo_aO_x \cdot Y(H_2O)$$

wherein a is 0.5-2, x is selected to satisfy the valence requirements of the bismuth and molybdenum and Y is a number such that the bound water is 5 to 40 weight percent of the total component, and optionally, the compound M and/or a support material, drying the slurry, and calcining to form the catalyst.

Such catalysts are specifically useful for production of acrylonitrile from propylene, ammonia and an oxygen-containing gas.

8 Claims, No Drawings

OXIDATION AND AMMOXIDATION CATALYST

BACKGROUND OF THE INVENTION

This invention relates to oxidation and/or ammoxidation catalysts containing the elements bismuth, molybdenum, antimony, vanadium and oxygen, and optionally containing one or more additional metal elements and to a method of preparing such catalysts. In another aspect, this invention relates to a process employing such catalysts.

It is well known that olefins can be oxidized to oxygenated hydrocarbons such as unsaturated aldehydes and acids, for example, acrolein and methacrolein, and acrylic and methacrylic acid. It is also well known that olefins can be ammoxidized to unsaturated nitriles such as acrylonitrile and methacrylonitrile. The value of such oxygenated hydrocarbons and unsaturated nitriles is generally well recognized with acrylonitrile being among the most valuable monomers available to the polymer industry for producing useful polymeric products.

Various catalytic processes are known for the oxidation and/or ammoxidation of olefins. Such processes commonly react an olefin or an olefin ammonia mixture with oxygen in the vapor phase in the presence of a catalyst. For the production of acrolein and acrylonitrile, propylene is the generally used olefin reactant and for the production of methacrolein and methacrylonitrile, isobutylene is the generally used olefin reactant.

Many catalysts are disclosed as suitable in the foregoing reactions. One such catalyst is described in Example 3 of U.S. Pat. No. 3,681,421. This catalyst employs oxides of antimony, vanadium, and at least one additional polyvalent metal which may be titanium in the proportion of 1 gram of antimony, 0.12–0.5 gram atoms of vanadium, and 0.25–0.5 gram atoms of titanium. Under the conditions of that example, a yield of 56% of acrylonitrile was obtained using proplyene, ammonia, air and steam as reactants.

Further, U.S. Pat. No. 4,062,885 discloses the preparation of phthalonitrile by ammoxidation of orthoxylene in the presence of a supported catalyst of the general formula $Bi_aSb_bMo_cV_dO_x$ wherein $a=1-20$, $b=1-10$, $c=0.1-15$ and $d=1-20$. Use of such a catalyst for oxidation or ammoxidation reactions involving unsaturated aliphatic hydrocarbons is not mentioned, however.

More recently, U.S. Pat. No. 4,093,558 discloses oxidation catalysts composed of the oxides of antimony, molybdenum, at least one of iron and vanadium, and, optionally, an additional element which may be bismuth. These catalysts are useful for manufacture of maleic anhydride from butane.

Preparation of ammoxidation catalysts by preforming bismuth molybdate and then mixing the preformed bismuth molybdate with other elements is disclosed in U.S. Pat. Nos. 4,040,978, 4,148,757 and 4,212,766.

It is well known that the economics of acrylonitrile manufacture dictate increasingly higher yields and selectivity of conversion of the reactants to acrylonitrile in order to minimize the difficulties attending purification of the product and handling of large recycle streams. Moreover, it is known that prior art catalysts frequently produce relatively large quantities of undesired oxygen-containing by-products such as $CO_2$, acrolein and/or acrylic acid which must be removed in purification of the acrylonitrile.

SUMMARY OF THE INVENTION

It is an object of this invention to provide a novel catalyst composition useful in the preparation of unsaturated aliphatic nitriles by ammoxidation of aliphatic olefins.

Yet another object is to provide a catalyst which is useful for oxidation of aliphatic olefins to the corresponding unsaturated aldehyde.

A more specific object of this invention is to provide a catalyst which gives surprisingly higher yields and selectivity of conversion of propylene, ammonia and air to acrylonitrile than do prior art catalysts.

It is a further object to provie a catalyst which minimizes the production of oxygenated by-products of acrylonitrile, such as $CO_2$, acrolein, acrylic acid and the like.

Still another object is to provide a catalyst which exhibits substantially its full activity immediately upon startup of an ammoxidation process, i.e., which requires no break-in period under ammoxidation conditions in order to exhibit its full efficiency in terms of activity and selectivity.

A further object of this invention is to provide a process for manufacture of such a catalyst.

In another aspect, it is an object of this invention to provide an ammoxidation process which employs such a catalyst.

To achieve these and other objects which will become apparent, a catalyst is provided having the empirical formula $BiMo_aV_bSb_cM_dO_x$ wherein $a=0.5-2$, $b=0.01-0.12$, $c=0.01-10$, $d=0-0.5$ and x is chosen to satisfy the valence requirements of the other elements present and in which M is one or more elements selected from Groups I-A, II-A, III-A, V-A, VI-A, I-B, IV-B, and VII-B of the Periodic Table of the Elements. According to the present invention, the catalyst is prepared by forming a slurry containing a vanadium component, an antimony component, a hydrophilic bismuth molybdate component and, optionally, one or more elements, and drying and calcining the resultant mixture.

As used herein, the term "hydrophilic bismuth molybdate" means a hydrophilic chemical compound of bismuth, molybdenum and oxygen and "hydrophilic" means 5 to 40 weight percent of the compound is bound water.

Bound water as used herein means water that is not released from the composition at room temperatures in a vacuum dessicator, but is released on heating at an elevated temperature, preferably between 150°–175° C.

The hydrophilic bismuth molybdate component can be prepared by various techniques, although, as will be seen in the specific embodiments that all methods known to the art for preparing bismuth molybdates do not achieve the hydrophilic bismuth molybdate of this invention.

A presently preferred method of preparing the hydrophilic bismuth molybdate component is by adding to an aqueous solution of bismuth oxide dissolved in nitric acid, an aqueous solution of molybdenum trioxide dissolved in ammonia, adjusting the pH of the resulting mixture to above 1.5 and up to 7, preferably up to 6.5 and more preferably from 2 to 5, and heating at an elevated temprature until the hydrophilic bismuth molybdate forms. The hydrophilic bismuth molybdate precipitate is filtered and washed. Generally, the solution mixture will be heated at a temperature of above 60° to 105° C. and for a period of 1 to 12 hours.

The molybdenum component can be introduced as a molybdenum salt instead of the oxide as indicated above. Useful salts are ammonium dimolybdate and heptamolybdate. Also, molybdic acid and molybdenum halides may be used. Likewise, the bismuth component can be introduced as bismuth metal in solution with nitric acid, as a salt, for example, bismuth acetates, citrates, nitrates, and triphenyls, and as bismuth halides when hydrolyzed.

Another method of preparing the hydrophilic bismuth molybdate component is by reacting bismuth nitrate with ammonia hydroxide and then reacting the resulting bismuth hydroxide with ammonium molybdate. This preparative technique, although requiring good dispersion and lengthy heating time, does not require recovery of the hydrophilic bismuth molybdate by filtration or the like prior to use as a component in catalyst preparations.

The hydrophilic bismuth molybdate component is preferably prepared in the absence of the other components. However, the bismuth molybdate component may, if desired, be prepared in situ in the presence of other elemental compounds and/or supports which do not interfere with the hydrophilic bismuth molybdate formation (such as their oxides). Thus, in preparing the catalyst the order of addition of the components will depend upon when the bismuth molybdate component is prepared.

The hydrophilic bismuth molybdate component is preferably combines as a wet cake, but may, if desired, be added as a pre-dried powder. Suitable drying temperatures would be room temperature to 300° C.

It is known that bismuth molybdate compounds may exist in alpha, beta and gamma forms or phases. An interesting and informative source of information on these forms of bismuth molybdate is found in *Journal of Solid State Chemistry*, Vol. 13, pp. 228-297 (1975), authored by Tu Chen and G. S. Smith. The alpha bismuth molybdate has the molecular formula $Bi_2(MoO_4)_3$, while the beta form is $Bi_2Mo_2O_9$ and the gamma form has the formula $Bi_2MoO_6$. Particularly, the preferred hydrophilic bismuth molybdate component has a molybdenum to bismuth atom ratio of 0.95-1.2, and contains predominantly the beta phase of bismuth molybdate on calcination above 570° C.

Although it is preferred to use the oxides of vanadium and antimony is preparing the catalyst, other antimony and vanadium-containing compounds may be employed. Exemplary of such antimony compounds are antimony trioxide, antimony tetroxide, antimony pentoxide and antimonic acid. Compounds which form an oxide of antimony after chemical reaction or calcination are also suitable. For example, metallic antimony, antimony hydroxides and antimony halides, such as antimony trichloride, tribromide and antimony pentachloride. Suitable vanadium compounds include vanadium oxides, such as vanadium pentoxide, tetroxide or trioxide, vanadium oxalate, ammonium metavanadate and vanadium halides. The vanadyl oxalate is preferably prepared in situ by reaction of the vanadium compound with oxalic acid, such as $V_2O_5$, $HVO_3$ or $NH_4VO_3$.

Following preparation of the hydrophilic bismuth molybdate component, it is mixed with the vanadium and antimony components in the desired proportions and well mixed, preferably in an aqueous slurry. At this point, a suitable catalyst support and/or one or more additional metal components may be added, if desired, as described below.

The aqueous slurry, if a slurry is employed, is then heated to remove the bulk of the aqueous phase. The concentrated slurry contains a certain amount of water and it is desirable to remove this water by some form of drying process to form a dry catalyst precursor. This can take the form of a simple oven-drying process in which the water-containing solid phase is subjected to a temperature that is sufficiently high to vaporize the water and completely dry the solid phase.

An alternate drying process which may be employed is the so-called spray-drying process in which water-containing solid phase particles are sprayed into contact with hot gas (usually air) so as to vaporize the water. The drying is controlled by the temperature of the gas and the distance the particles travel in contact with the gas. It is generally undesirable to adjust these parameters to achieve too rapid drying as this results in a tendency to form dried skins on the partially dried particles of the solid phase which are subsequently ruptured as water occluded within the particles vaporizes and attempts to escape. By the same token, it is desirable to provide the catalyst in a form having as little occluded water as possible. Therefore, where a fluidized bed reactor is to be used and microspheroidal particles are desired, it is advisable to choose the conditions of spray-drying with a view of achieving substantially complete drying without particle rupture.

Following the drying operation, the catalyst precursor is calcined to form the catalyst. The calcination process is usually conducted in air at essentially atmospheric pressure and at a temperature of about 525° C. to about 800° C., such as from about 550° C. to about 650° C. The time to complete the calcination can be anything up to 10 hours, but for most purposes, the calcination need take only from about 1 to 2 hours.

In some applications, it may be advantageous to include in the catalyst a support material which may or may not be active catalytically but which functions by providing a large surface area for the catalyst and by creating a harder and more durable catalyst for use in the highly abrasive environment of a fluidized bed reactor. This support material can be any of those commonly proposed for such use such as, for example, silica, zirconia, alumina, titania, antimony pentoxide sol or other oxide substrates. From the point of view of availability, cost and performance, silica is usually a satisfactory support material and is preferably in the form of silica sol for easy dispersion.

The proportions in which the components of the supported catalyst are present can vary widely but it is usually preferred that the support provides from 10 to 90% and most preferably about 35 to 60% by weight of the total combined weight of the catalyst and the support. To incorporate a support into the catalyst, the support material is preferably combined with the slurry containing the active components discussed above.

As has been stated, catalysts according to this invention are those having the empirical formula $BiMo_aV_bSb_cM_dO_x$, where a is from 0.5-2, b is from 0.01-0.12, c is from 0.01-10, d is from 0-0.5 and x is taken to satisfy the valence requirements of the other elements present. In more preferred embodiments of such catalysts, a is from 0.7-1.5, b is from 0.02-0.05, c is from 0.1-3 and d is from 0-0.2.

In many instances, it may be desirable to modify the catalyst physical properties or the spectrum of by-products made in, for example, ammoxidation processes in which these catalysts are employed. Further, it may be desirable to modify the physical properties of the catalyst somewhat. To this end, one or more additional elements may be incorporated into the catalyst formulation. Depending upon the particular property sought to be modified, suitable additive elements may include one or more elements selected from Groups I-A, II-A, III-A, V-A, VI-A, I-B, IV-B, VI-B and VII-B of the Periodic Table of Compound or compounds of the desired element(s) are conveniently added to the mixture containing the active bismuth molybdate, vanadium and antimony components, either before or after addition of the silica sol or other support material, if a support material is employed.

Specifically preferred among the modifying additive elements are potassium, calcium, magnesium, boron, thallium, arsenic, phosphorus, selenium, tellurium, silver, titanium, zirconium, tungsten and manganese, and antimony although other modifier elements may be employed.

The catalyst preparation of the invention yields a catalyst that is particularly useful in the production of acrylonitrile from propylene and in which follows specific reference is made to that process although it should be understood that the described catalyst is also useful for ammoxidation of other olefins and for oxidation of aliphatic olefins to aldehydes and acids.

In the most frequently used ammoxidation processes, a mixture of olefin, ammonia and oxygen (or air) is fed into a reactor and through a bed of catalyst particles. The reaction temperature is usually in the range of 400° C. to 550° C., and preferably 450° C. to 525° C., and the pressure is 1 to 6 atmospheres (100 to 600 kPa). The ammonia and olefin are required stoichiometrically in equimolar amounts, but it is usually necessary to operate with a molar ratio of ammonia to olefin in excess of 1 to reduce the incidence of side reactions. Likewise, the stoichiometric oxygen requirement is 1.5 times the molar amount of olefin. The feed mixture is commonly introduced into the catalyst bed at a W/F (defined as the weight of the catalyst in grams divided by the flow of reactant stream in ml/sec. at standard temperature and pressure) in the range of 2 to about 15, preferably from about 4 to about 10.

The ammoxidation reaction is exothermic and for convenience in heat distribution and removal the catalyst bed is desirably fluidized; however, fixed catalyst beds may be employed with alternative heat removal means such as cooling coils within the bed.

The catalyst prepared by the process of the present invention is particularly well adapted for use in such a process and in which follows its effectiveness and advantages over prior art catalysts are demonstrated in the context of that process.

A measure of the hydrophilic character of the bismuth molybdate is obtained as follows:

(a) A 1 to 10 gram sample of bismuth molybdate sample is vacuo-dried at room temperature in a vacuum dessicator until a constant weight is obtained, typically 24–48 hours.

(b) The vacuo-dried sample is heated at 160°–170° C. for 16–24 hours and then weighed at room temperature. The Weight of Bound Water is the weight of the vacuo-dried sample minus the weight of the heated sample.

(c) The sample is then calcined at 450° C. to remove ammonium nitrate and weighed at room temperature to give the Weight of Calcined Sample.

(d) The "% B.W." is the percent Bound Water in the sample and is defined as:

$$\frac{\text{Weight of Bound Water}}{(\text{Weight of Bound Water}) + (\text{Weight of Calcined Sample})} \times 100\%$$

SPECIFIC EMBODIMENTS

As has been stated above, the catalyst of the invention has the empirical formula $BiMo_aV_bSb_cM_dO_x$, wherein $a=0.5-2$, $b=0.01-0.12$, $c=0.01-10$, $d=0-0.5$ and x is a number taken to satisfy the valence requirements of the other elements present in the catalyst, optionally dispersed on a finely divided support which represents from 10 to 90% of the supported catalyst weight. In the examples that are presented below, specific compositions within this range were prepared and employed as catalysts in the ammoxidation of propylene to produce acrylonitrile.

The hydrophilic bismuth molybdate component precursor used to prepare the catalysts of the invention has the empirical formula $BiMo_aO_x \cdot Y(H_2O)$ wherein a is 0.5 to 2, x is a number taken to satisfy the valence requirements of the bismuth and molybdenum and Y is 5 to 40 weight percent of the composition.

As used in the following examples, the following terms are defined in the following manner:

1. "W/F" is defined as the weight of the catalyst in grams divided by the flow rate of reactant stream in ml/sec. measured at S.T.P.

2. "Propylene ($C_3H_6$) conversion" is defined as:

$$\frac{\text{Mols } C_3H_6 \text{ in feed} - \text{mols } C_3H_6 \text{ in effluent}}{\text{Mols } C_3H_6 \text{ in feed}} \times 100\%$$

3. "Acrylonitrile (AN) selectivity" is defined as:

$$\frac{\text{Mols AN in effluent}}{\text{Mols } C_3H_6 \text{ converted}} \times 100\%$$

4. "Acrylonitrile (AN) yield" is defined as:

$$\frac{\text{Mols AN formed}}{\text{Mols } C_3H_6 \text{ feed}} \times 100\%$$

In the following examples, unless otherwise noted, the catalysts of the examples were evaluated to determine acrylonitrile selectivity and yield and propylene conversion in a fluidized bed reaction vessel having an inside diameter of about 12.8 millimeters. Approximately 25 grams of catalyst was used in each case. A reactant mixture of 17–17.8 volume % $O_2$, 7.6–8.3 volume % propylene ($C_3H_6$), 8–9% volume % $NH_3$, and the balance helium was passed upward through the catalyst bed at a rate sufficient to give the value of W/F shown in the experimental results for each example. The temperatures shown in the examples are expressed in degrees Celsius, and in each instance the pressure at which the reaction was carried out was 207 kPa unless otherwise noted.

EXAMPLE 1

A series of catalysts according to the present invention were prepared by the following technique.

Bismuth Molybdate Component 171 grams of molybdenum trioxide (MoO$_3$) were dissolved in a mixture of 433 ml of water and 215 ml of 57% ammonium hydroxide, added to a solution of 251.7 grams of bismuth trioxide (Bi$_2$O$_3$) in 833 ml of water and 367 ml of 70% nitric acid with stirring. The pH of the resulting mixtures were adjusted to between 1 and 6.5 using ammonium hydroxide and heated for approximately 2 hours at 100° C. The bismuth molybdate precipitate was filtered and washed with approximately 500 ml of water.

The hydrophilic nature of each of the bismuth molybdate precipitates was measured by placing a preweighed sample (1 to 2 grams) in preweighed crucibles and dried at ambient temperature in a vacuum dessicator. Each sample was then weighed and the water loss calculated. Each sample was then heated for 16 hours at 165° C. and then cooled in a dessicator and weighed. Each sample was then heated to 450° C. to remove any ammonia nitrate and weighed to find the dry weight of the precipitate.

Catalyst

To selected quantities of silica sol containing 40% silica adjusted to a pH of 1.0–1.2 with 70% nitric acid were added the above prepared bismuth molybdate compounds and the pH was maintained from 1.0–1.2. Selected quantities of vanadium pentoxide and antimony trioxide were added to the bismuth molybdate-silica mixtures with mixing. Each mixture was heated at 100° C., spray-dried and then calcined in air at 500°–600° C. for 1 hour to obtain the catalysts.

Each of the above prepared catalysts having the empirical formula BiMo$_{1.1}$V$_{0.023}$Sb$_{0.24}$O$_x$ was charged into the reaction vessel and evaluated for propylene ammoxidation as described above.

Specific variables and results obtained for each prepared bismuth molybdate precursor and catalyst are given in Table 1.

EXAMPLE 2

A catalyst composition having an empirical formula like the catalysts of Example 1 was prepared by the procedure of Example 1, except that the bismuth molybdate component was prepared by mixing bismuth oxide and molybdenum trioxide in water at a pH of 3.5. A 0.593 gram wet sample of the bismuth molybdate precipitate weighed 0.387 gms on drying in vacuo, weighed 0.377 gms on drying at 165° C., and 0.372 gms on calcining. The % B.W. for this sample was 3%. The completed catalyst as used for propylene ammoxidation at 470° C. and at a 5 W/F gave 51% AN yield, 65% AN selectivity and 78% conversion.

From this example, it is readily apparent that bismuth molybdates prepared as taught in the prior art, as exemplified by U.S. Pat. No. 4,212,766, column 4, lines 64–68, from individual oxides of the elements does not provide the hydrophilic bismuth molybdate of this invention nor the improved catalytic activity of a finished catalyst based thereon.

EXAMPLE 3

Example 1 is repeated, except that the vanadium and antimony is added as a preformed vanadium antimonate (VSb$_2$) and the catalysts are represented by the empirical formula $$Bi_{10}Mo_{11}(VSb_2)_{1.75}O_x$$

Characteristics of each run and the results are given in Table II.

TABLE II

| Run | pH$^a$ | Temp. | W/F | % AN Yield | % C$_3$ Conversion |
|---|---|---|---|---|---|
| A | 1.1 | 465 | 5 | 54 | 83 |
| B | 1.3 | 476 | 5 | 50 | 81 |
| C | 6.5 | 475 | 4 | 70 | 95 |

$^a$Reaction pH for bismuth molybdate component.

The above example clearly shows the effectiveness of improving catalysts regardless of the additional elements incorporated (i.e., a vanadium antimonate component vs a vanadium component and an antimony component). Furthermore, the effectiveness of use of

TABLE I

| | | BISMUTH MOLYBDATE COMPONENT | | | | |
|---|---|---|---|---|---|---|
| RUN | REACTION pH | WEIGHT WET ppt (gms) | VACUO-DRIED WEIGHT (GMS) | 165° - DRIED WEIGHT (GMS) | CALCINED WEIGHT (GMS) | % B.W. |
| A | 1.0 | 1.679 | 1.104 | 1.070 | 1.062 | 3 |
| B | 1.5 | 6.081 | 4.268 | 4.188 | 4.163 | 2 |
| C | 2.0 | 1.221 | 0.471 | 0.347 | 0.344 | 26 |
| D | 2.8 | 1.159 | 0.525 | 0.388 | 0.385 | 26 |
| E | 3.5 | 1.635 | 0.584 | 0.448 | 0.444 | 23 |
| F | 5.0 | 1.120 | .468 | 0.369 | 0.359 | 22 |
| G | 6.5 | 4.075 | 1.647 | 1.338 | 1.140 | 21 |
| H | 6.5/3.5$^a$ | 3.786 | 1.512 | 1.007 | 0.998 | 34 |

| | PROPYLENE AMMOXIDATION | | | | |
|---|---|---|---|---|---|
| RUN | TEMP. | W/F | % AN YIELD | % AN SELECTIVITY | % C$_3$ CONVERSION |
| A | 470 | 6 | 32 | 53 | 59 |
| B | 475 | 7 | 42 | 60 | 70 |
| C | 470 | 5 | 70 | 74 | 95 |
| D | 480 | 7.5 | 73 | 77 | 95 |
| E | 470 | 5 | 74 | 76 | 97 |
| F | 475 | 6 | 74 | 78 | 95 |
| G | 470 | 5 | 68 | 78 | 87 |
| H | 475 | 6 | 74 | 77 | 96 |

$^a$Heated at 6.5 for 2 hours and then at 3.5 for 3 hours.

the hydrophilic bismuth molybdate of this invention is shown by Run C.

EXAMPLE 4

A catalyst having the empirical formula like the catalysts of Example 1 was prepared using an alternate preparation procedure for the bismuth molybdate. In this alternate procedure 251.7 gms $Bi_2O_3$ was dissolved in 367 ml 70% nitric acid plus 900 ml water. To it was added a solution of 372 ml of 57% ammonium hydroxide and 1400 mls of water resulting in a white precipitate which was washed with 1000 ml of water by decantation. To this precipitate was added 171 gms of molybdenum trioxide and 116 mls of 57% ammonium hydroxide, the mixture was heated at 80°–85° C. for 3 hours, the pH was dropped to 3.5 with 70% nitric acid and the mixture cooked an additional 3 hours at 80°–85° C. A 2.082 gm sample of wetcake was obtained by filtration, on vacuo-drying it weighed 1.462 gms, on drying at 165° C. it weighed 1.274 gms, and 1.244 gms on calcining at 450° C. The % B.W. for this sample was 13%. To prepare the catalyst, the bismuth molybdate slurry was pH adjusted to 1.8 with 70% $HNO_3$, and added to it was 1300 gms of silica sol (40%) pH adjusted to 1.8, 2.2 gms of $V_2O_5$ and 37 gms $Sb_2O_3$. The catalyst slurry was then treated as in Example 1. The completed catalyst as used for ammoxidation at 475° C. and at a 6 W/F gave 72% AN yield, 75% AN selectivity and 96% $C_3H_6$ conversion.

From this example, it is clear that alternate preparations of the hydrophilic bismuth molybdate component can be used.

What is claimed is:

1. A catalyst for oxidation and ammoxidation of hydrocarbons consisting essentially of catalytic elements having the empirical formula $$BiMo_aV_bSb_cM_dO_x$$

wherein a is from 0.5 to 2, b is from 0.01 to 0.12, c is from 0.01 to 10, d is from 0 to 0.5, and x is taken to satisfy the valence requirements of the other elements present and wherein M is one or more elements selected from Groups I-A, II-A, III-A, V-A, VI-A, I-B, IV-B, VI-B and VII-B of the Periodic Table, said catalyst being prepared by forming a mixture containing a vanadium component, an antimony component, a hydrophilic bismuth molybdate component having the empirical formula.

$$BiMo_aO_x \cdot Y(H_2O)$$

wherein a is from 0.5 to 2, x is taken to satisfy the valence requirement of the other elements present and Y is a number such that the bound water is 5 to 40 weight percent of the total component forming said mixture into dry particles, and calcining at a temperature of from 500° to 850° C.

2. A catalyst according to claim 1 wherein M is one or more elements selected from potassium, calcium, manganese, boron, thallium, arsenic, phosphorus, selenium, tellurium, silver, titanium, zirconium, tungsten, and antimony.

3. A catalyst according to claim 2 wherein a is from 0.7 to 1.5, b is from 0.02 to 0.05, c is from 0.1 to 3 and d is from 0 to 0.5.

4. A catalyst according to claim 2 wherein said mixture is an aqueous slurry.

5. A catalyst according to claim 4 wherein said bismuth molybdate component is formed prior to forming said slurry.

6. A catalyst according to claim 4 wherein a support material comprising from about 10 to about 90% of the total weight of said catalyst is added to said slurry.

7. A catalyst according to claim 6 wherein said support material comprises from about 35 to about 60% of the total weight of said catalyst.

8. A catalyst according to claim 7 wherein said support material is silica.

* * * * *